US011726649B2

(12) United States Patent
Finelli et al.

(10) Patent No.: US 11,726,649 B2
(45) Date of Patent: Aug. 15, 2023

(54) SYSTEMS AND METHODS FOR RENDERING DIGITAL IMAGES

(71) Applicant: CLIENT OUTLOOK INC., Waterloo (CA)

(72) Inventors: Bruno Monteiro Finelli, Waterloo (CA); Scott Alexander Bohdanow, Kitchener (CA); Neil Edmund James Hunt, Waterloo (CA); Steven Andrew Rankin, Waterloo (CA)

(73) Assignee: MACH7 TECHNOLOGIES CANADA INC., Toronto (CA)

( * ) Notice: Subject to any disclaimer, the term of this patent is extended or adjusted under 35 U.S.C. 154(b) by 0 days.

(21) Appl. No.: 17/419,929

(22) PCT Filed: Jan. 10, 2020

(86) PCT No.: PCT/CA2020/050026
§ 371 (c)(1),
(2) Date: Jun. 30, 2021

(87) PCT Pub. No.: WO2020/142849
PCT Pub. Date: Jul. 16, 2020

(65) Prior Publication Data
US 2022/0043550 A1    Feb. 10, 2022

Related U.S. Application Data

(60) Provisional application No. 62/791,254, filed on Jan. 11, 2019.

(51) Int. Cl.
*G06F 3/0485*    (2022.01)
*G06F 3/0354*    (2013.01)
(Continued)

(52) U.S. Cl.
CPC ........ *G06F 3/0485* (2013.01); *G06F 3/03543* (2013.01); *G06F 3/04845* (2013.01);
(Continued)

(58) Field of Classification Search
CPC ............... G06F 3/0485; G06F 3/03543; G06F 3/04845; G06F 3/14; G16H 30/20;
(Continued)

(56) References Cited

U.S. PATENT DOCUMENTS

2008/0155461 A1    6/2008  Ozaki
2014/0181733 A1    6/2014  Oyanagi et al.
(Continued)

OTHER PUBLICATIONS

WIPO, Written Opinion and International Search Report for PCT Application No. PCT/CA2020/050026 dated Apr. 14, 2020.
(Continued)

*Primary Examiner* — Koosha Sharifi-Tafreshi
(74) *Attorney, Agent, or Firm* — Norton Rose Fulbright Canada LLP (57) ABSTRACT

Systems and methods for presenting a sequence of medical images are provided herein. A use provides an input which indicates that additional frames are to be displayed. Frames from the sequence are displayed in succession, without skipping the display of any frames, based on a frame rate determined by an input provided by a user.

16 Claims, 7 Drawing Sheets

(51) Int. Cl.
    *G06F 3/04845*    (2022.01)
    *G06F 3/14*       (2006.01)
    *G16H 30/20*      (2018.01)

(52) U.S. Cl.
    CPC .............. *G06F 3/14* (2013.01); *G16H 30/20*
                      (2018.01); *G09G 2380/08* (2013.01)

(58) Field of Classification Search
    CPC .... G16H 30/40; G16H 30/00; G09G 2380/08;
                G09G 2354/00; G09G 2370/022; G09G
                                5/34; G09G 2340/0435
    See application file for complete search history.

(56) References Cited

U.S. PATENT DOCUMENTS

2015/0052470 A1*  2/2015  Kim .................. G16H 50/20
                                                      715/771
2016/0349957 A1* 12/2016  Lee .................. G06F 3/0482

OTHER PUBLICATIONS

Tan et al. "Improving mouse pointing/or radiology tasks" Medical Imaging 2009: Image Perception, Observer Performance, and Technology Assessment, vol. 7263, International Society for Optics and Photonics, 2009.

* cited by examiner

SYSTEMS AND METHODS FOR RENDERING DIGITAL IMAGES

CROSS-REFERENCE TO RELATED APPLICATIONS

This application claims priority to U.S. Provisional Patent Application No. 62/791,254, filed on Jan. 11, 2019, the entire contents of which are incorporated by reference herein.

FIELD

This relates to displaying digital images, and in particular to navigating through sequences of images.

BACKGROUND

Modern tasks are becoming increasingly digitized. For example, medical professionals rely heavily on digitized images in evaluating patient health. The analysis of digital images by healthcare professionals plays an integral role in patient diagnosis and patient care overall.

As reliance on digital technologies increases, so too does the quantity of data being stored digitally. In particular, with storage being ubiquitous, increasing quantities of images with increasing resolution are being stored.

It can be difficult to view or navigate through large quantities of digital images. In particular, technicians and medical professionals are often required to scroll through vast quantities of images, which can cause repetitive strain injuries due to poor ergonomics of input devices. It would be desirable to conveniently navigate through digital images.

SUMMARY

In accordance with one aspect of the invention, there is provided a method of presenting a plurality of frames from a sequence of medical images at a client device, the method comprising: displaying, on a display device, a first frame from a sequence of images; receiving, via an input device, an indication to display at least second and third adjacent frames from the sequence of images; determining a frame rate for displaying the at least second and third adjacent frames based on the indication received from the input device; displaying, on the display device, the at least second and third adjacent frames in accordance with the frame rate.

In some embodiments, the at least second and third adjacent frames immediately succeed the first frame in the sequence of images.

In some embodiments, the at least second and third adjacent frames immediately precede the first frame in the sequence of images.

In some embodiments, the frame rate for displaying the at least second and third adjacent frames is based on a characteristic associated with the indication received from the input device.

In some embodiments, the indication is a command to scroll in a first direction at a first rate.

In some embodiments, the indication is a movement of a pointing device in a first direction at a first speed.

In some embodiments, the indication is a movement of a pointing device outside of a boundary of the first frame in a user interface.

In some embodiments, the at least second and third frames are displayed at a frame rate less than or equal to a predefined maximum frame rate when the pointing device is outside of the boundary of a frame being displayed.

In some embodiments, the indication is a pressing and holding of a key on the input device.

In some embodiments, the received indication is a first indication, and the method comprises: receiving a second indication subsequent to the first indication.

In some embodiments, the method further comprising: modifying the frame rate based on the second indication.

According to another aspect, there is provided a computing device for presenting frames of a sequence of medical images, the computing device comprising: a processor; a display device; an input device; a memory having stored thereon processor-executable instructions for: displaying, on the display device, a first frame from a sequence of images; receiving, via the input device, an indication to display at least second and third adjacent frames from the sequence of images; determining a frame rate for displaying the at least second and third adjacent frames based on the indication received from the input device; displaying, on the display device, the at least second and third adjacent frames in accordance with the frame rate.

According to another aspect, there is provided a system for presenting a sequence of medical images, the system comprising: a server comprising a processor and a memory storing a sequence of medical images comprising a plurality of frames; and a client device comprising: a processor; a network interface; a display device; an input device; a memory having stored thereon processor-executable instructions for: receiving, via the network interface, two or more frames of the sequence of medical images; displaying, on the display device, a first frame from the received sequence of images; receiving, via the input device, an indication to display at least second and third adjacent frames from the received sequence of images; determining a frame rate for displaying the at least second and third adjacent frames based on the indication received from the input device; and displaying, on the display device, the at least second and third adjacent frames in accordance with the frame rate.

BRIEF DESCRIPTION OF DRAWINGS

In the drawings, which depict example embodiments.

The drawings illustrate example embodiments and the scope of the invention is not limited to specific embodiments depicted in the drawings.

DETAILED DESCRIPTION

Figure 1:
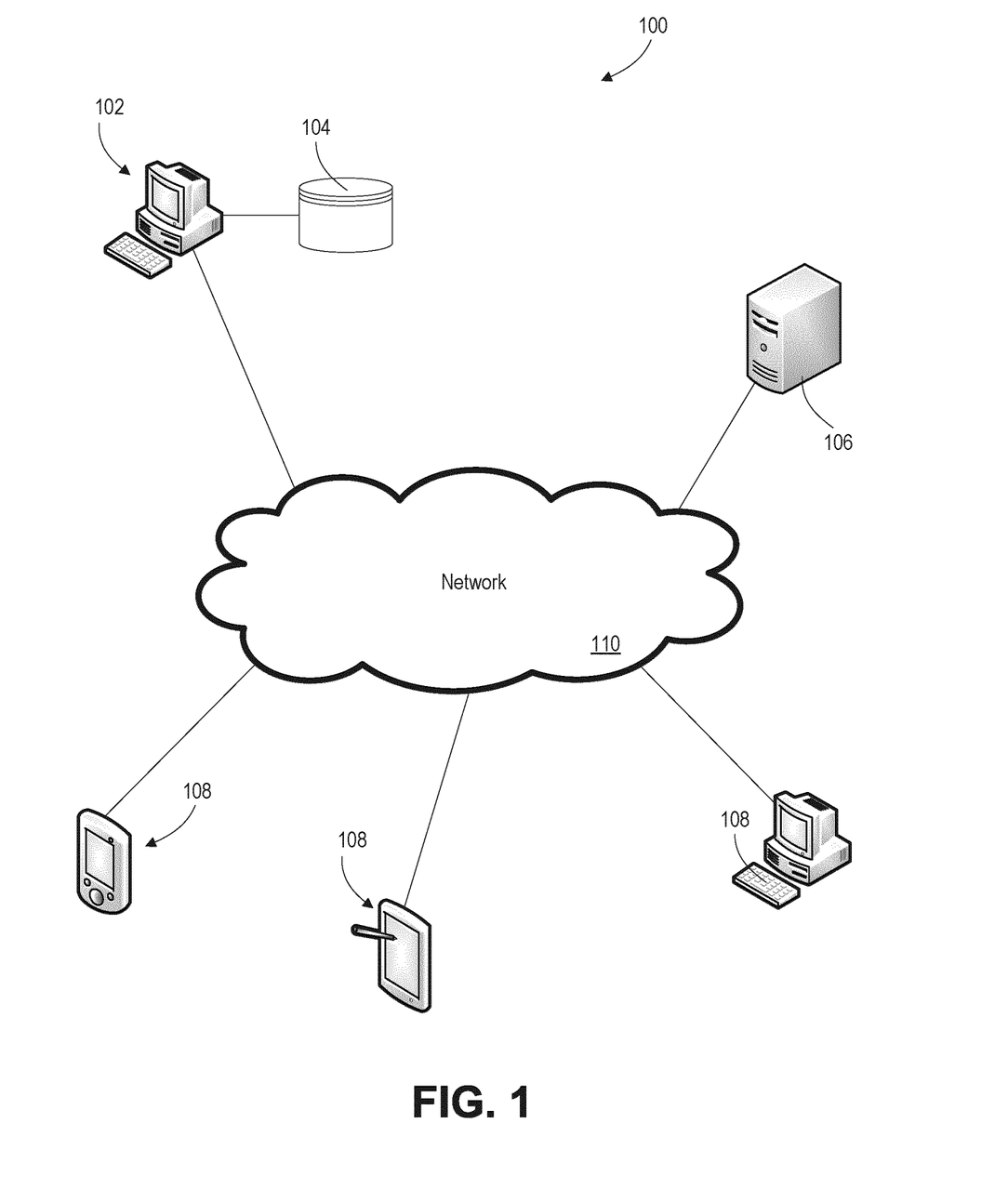
FIG. 1 is a block diagram depicting components of an example computing system.

FIG. 1 is a block diagram depicting components of an example computing system. Components of the computing system are interconnected to define a content navigation system 100. As used herein, the term content navigation system refers to a combination of hardware devices configured under control of software, and interconnections between such devices and software. Such systems may be operated by one or more users.

As depicted, content navigation system 100 includes at least one server 102 with a data storage 104 such as a hard drive, array of hard drives, network-accessible storage or the like; at least one web server 106 and a plurality of client computing devices 108. Server 102, web server 106 and client computing devices 108 are in communication by way of a network 110. More or fewer of each device are possible relative to the example configuration depicted in FIG. 1. Data storage 104 may contain, for example, a plurality of sets of medical diagnostic images. For example, the medical diagnostic images may include sets of digital images taken from computerized tomography (CT) scans, magnetic resonance imaging (MRI) scans, or the like. Such scans typically result in a sequence of images as the scanning apparatus scans across a given area. Such sequences of images are spatially and/or temporally linked.

The network 110 may include one or more local-area networks or wide-area networks, such as IPv4, IPv6, X.25, IPX compliant or similar networks, including one or more wired or wireless access points. The networks may include one or more local-area networks (LANs) or wide-area networks (WANs), such as the internet. In some embodiments, the networks are connected with other communications networks, such as GSM/GPRS/3G/4G/LTE networks.

As shown, server 102 and web server 106 are separate machines, which may be at different physical or geographical locations. However, server 102 and web server 106 may alternatively be implemented in a single physical device.

As will be described in further detail, server 102 may be connected to a data storage 104, which may include records containing information associated with an individual (e.g. a user, a patient, a customer, or the like). Such information may include, for example, medical information associated with the user, including medical images associated with the user.

Web server 106 hosts a website 400 accessible by client computing devices 108. Web server 106 is further operable to exchange data with server 102 such that data associated with a user (e.g. medical records and/or digital images) can be retrieved from server 102 and displayed on the website, or entered by way of the website and transmitted to server 102 for storage.

Server 102 and web server 106 may be based on Microsoft Windows, Linux, or other suitable operating systems.

Client computing devices 108 may be, for example, personal computers, smartphones, tablet computers, or the like, and may be based on any suitable operating system, such as Microsoft Windows, Apple OS X or iOS, Linux, Android, or the like. In some embodiments, client computing devices 108 may be associated with one or more of a customer, a patient, a medical office, an individual health practitioner, or other parties.

Figure 2:
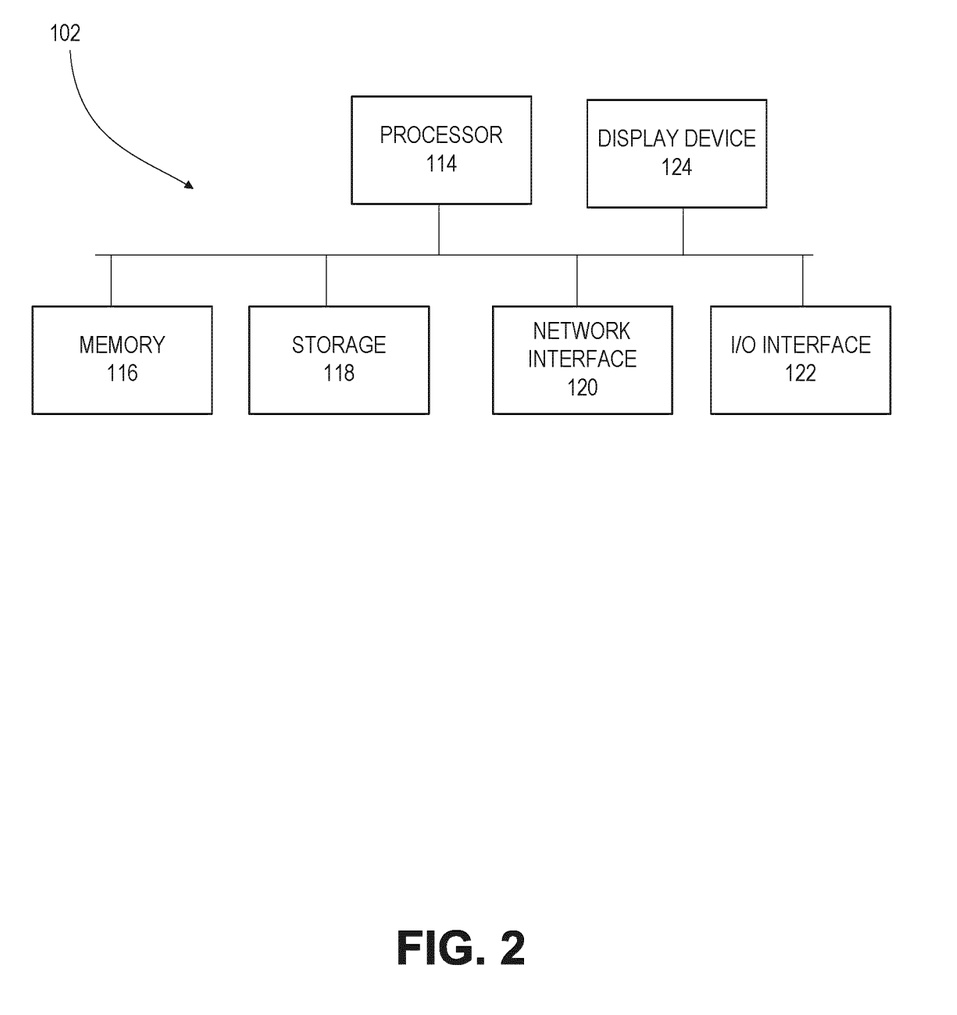
FIG. 2 is a block diagram depicting components of an example server or client computing device.

FIG. 2 is a block diagram of components of an example server 102, 106 or client computing device 108. As depicted, each server 102, 106 and client computing device 108 includes a processor 114, memory 116, persistent storage 118, network interface 120 and input/output interface 122.

Processor 114 may be an Intel or AMD x86 or x64, PowerPC, ARM processor, or the like. Processor 114 may operate under control of software loaded in memory 116. Network interface 120 connects server 102, 106 or client computing device 108 to network 110. I/O interface 122 connects server 102, 106 or client computing device 108 to one or more storage devices (e.g. storage 104) and peripherals such as keyboards, mice, pointing devices, USB devices, disc drives, display devices 124, and the like.

Software may be loaded onto server 102, 106 or client computing device 108 from peripheral devices or from network 106. Such software may be executed using processor 114.

Figure 3:
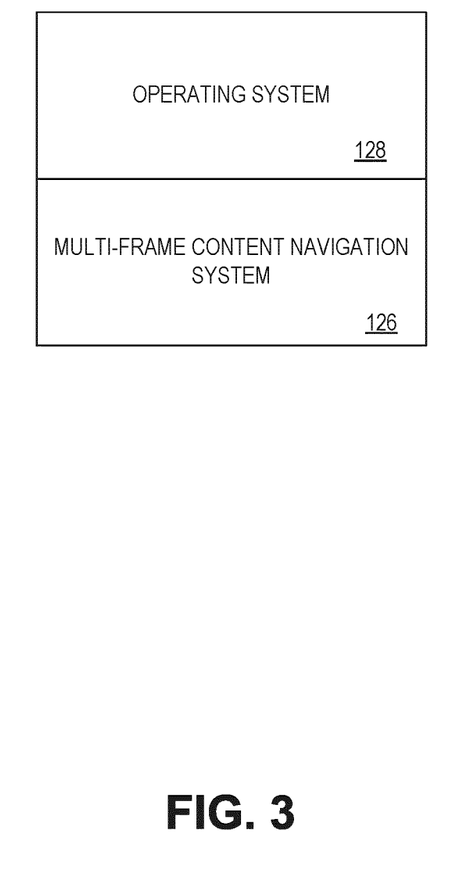
FIG. 3 depicts a simplified arrangement of software at a server or client computing device.

FIG. 3 depicts a simplified arrangement of software at a server 102 or client computing device 108. The software may include an operating system 128 and application software, such as multi-frame content navigation system 126. Multi-frame content navigation system 126 (hereinafter "navigation system 126") is configured to accept inputs which include user information and a sequence of digital images. In some embodiments, the sequence of digital images is associated with the user or a patient.

Figure 4:
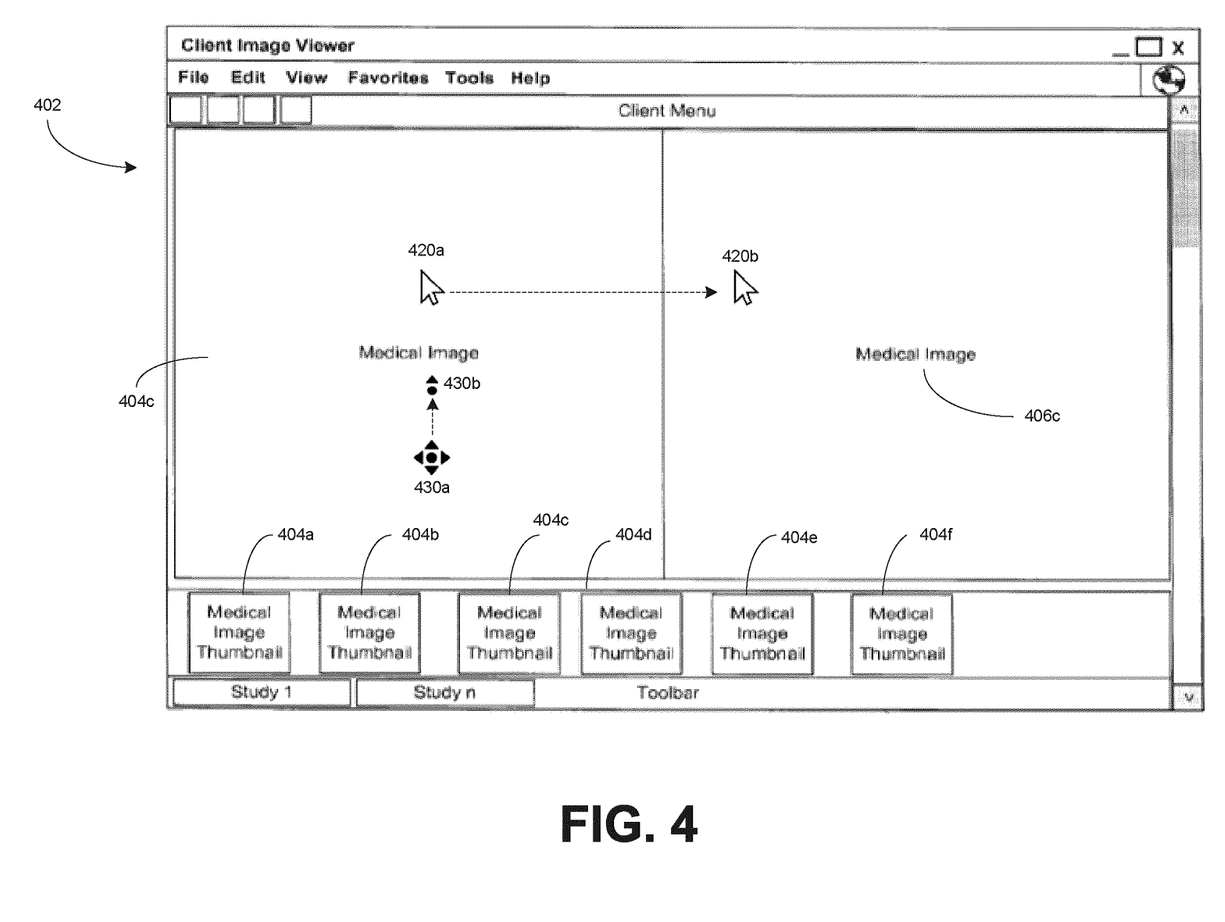
FIG. 4 depicts an example user interface presented at client device by a navigation system.

Navigation system 126 may cause a user interface 400 to be displayed on a display of client device 108 for presentation to a user. FIG. 4 depicts an example user interface 402 presented at client device 108 by navigation system 126. In some embodiments, the user interface may be presented as a website 400 or downloaded from web server 106 each time the navigation system 126 is invoked (e.g. via the entering of a uniform resource locator (URL)) within a web browser executing on client device 108. User interface 400 may also be presented as an app on a mobile device, desktop device, or other suitable computing device. In some embodiments, executing the navigation system 126 via a web browser may keep the navigation system 126 software up to date and avoid the need to formally install the navigation system locally on client device 108.

As shown in FIG. 4, navigation system 126 is operable to display an image 404c in user interface 402. In some embodiments, image 404c is a medical image which is part of a sequence of medical images (collectively referred to as sequence 404). As described herein after, individual images from the image sequence 404 are commonly referred to as frames. User interface 402 may display thumbnail previews of a plurality of frames 404a, 404b, 404c, 404d, 404e, 404f in sequence 404. As depicted, user interface 402 includes a display of frame 406c. In some embodiments, frame 406c is a related image from a different perspective. For example, frames 404a-404f may represent a front view, while frames 406a-406f may represent a side or top view. Although FIG. 4 depicts a user interface in which both frames 404c and 406c are displayed simultaneously, it is contemplated that some embodiments may display only one set of image sequences 404, and other embodiments may display 3 or more related image sequences simultaneously. Moreover, although FIG. 4 depicts image sequence 404 as including 6 frames, it is contemplated that an image sequence 404 may include less than 6 or substantially more than 6 frames.

In some embodiments, image sequence 404 includes a plurality of medical images (sometimes referred to as an image series). For example, image sequence 404 may include a plurality of images or frames taken during a CT or MRI scan. As such, each frame 404a, 404b, . . . 404f may form a group of spatially related, anatomically contiguous medical images of a patient which a healthcare practitioner or other user may subsequently review or analyze.

Often, viewing such sequences of images requires that the user review the plurality of frames contained within image sequence 404. The act of reviewing a series of frames is referred to herein as navigation. Often, healthcare practitioners are required to navigate through frames of an image sequence 404 in order to diagnose or otherwise make determinations as to the patient's health or physical condition.

It is imperative that during navigation, a professional reviewing the frames is able to focus on the content on the frames without distraction. Thus, a seamless interface in which the user can make commands without distracting themselves from the displayed frames is desirable. Moreover, it is important for the professional to be able to view each and every frame in a sequence in order to be exposed to the most image data possible. In addition, it is important that the professional be able to review the frames without incurring injury or soreness through excessive scrolling or otherwise use of input devices. In some embodiments, a sequence of medical images may contain over 1000 frames (e.g. a CT scan moving through a cross-sectional area of a patient).

Medical images are captured by medical devices and may be stored in data storage 104. Data storage 104 may be located remotely from a client device 108. Sequences of medical images may be accessed and viewed on computing device 108 through a website provided by web server 106. The performance of conventional websites may, at times, be insufficient for the presentation of frames from a medical image sequence.

For example, conventional systems allow a user to navigate through a sequence of frames by receiving a command to view a different frame in the sequence of images. A user may press a button on a keypad device or click with a pointing device to load a different frame. Such inputs are typically linear in nature. That is, a single press or click of a button, or rotation of a scroll wheel on a mouse, corresponds to a single, individual increment. The receipt of individual commands to load an individual frame in the sequence of frames is cumbersome, particularly in situations where the sequence of images includes thousands of images. Further, the practitioner may wish to view the frames with varying display frequencies. For example, in a scan of a user's head, a practitioner reviewing the frames may wish to quickly scan through images of the patient's lower jaw if they are only concerned with the condition of the patient's nose (and may wish to slow down the frequency of displaying the frames which are in and around the patient's nose).

Moreover, in conventional systems, if a user attempts to view multiple frames in quick succession, the frame rate supported by the web browser may be insufficient to view each individual image. That is, the user interface may only display certain frames from the sequence of images while skipping other frames, rather than presenting each individual frame. For example, the user interface may only display every 5$^{th}$ frame in a sequence of 1000 frames as a user navigates through the sequence of images. This is problematic, as the practitioner reviewing the medical image data should be exposed to the maximum amount of image data in order to glean maximum information and make the most informed decisions possible.

Figure 5:
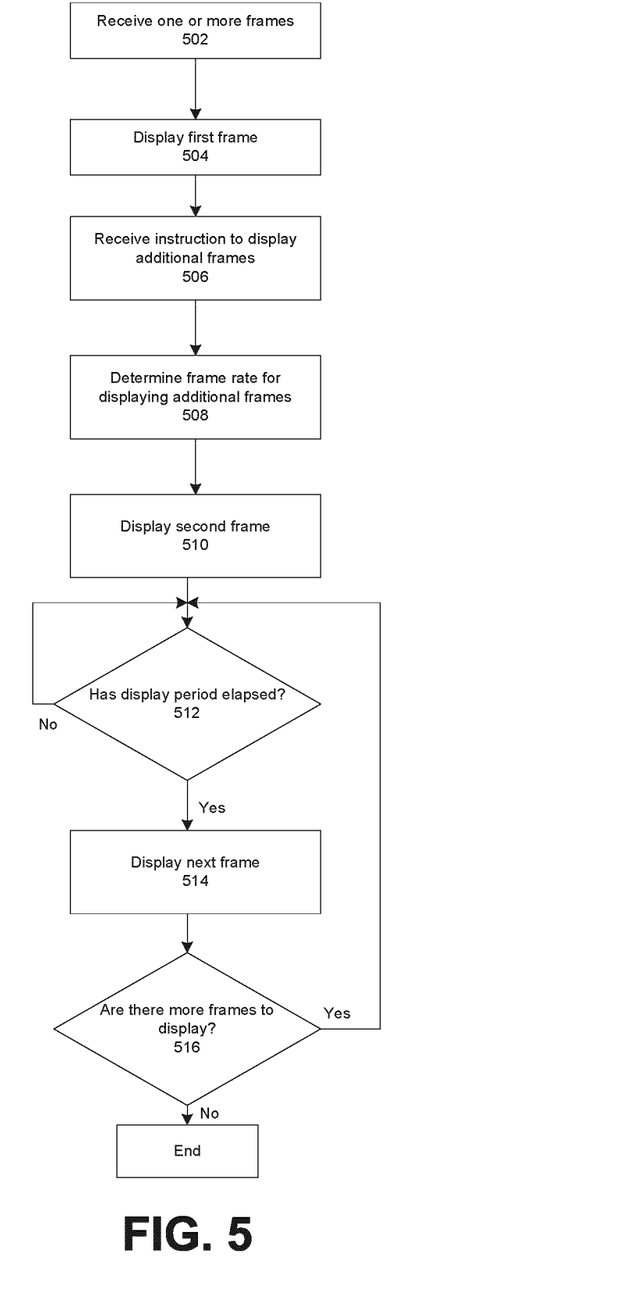
FIG. 5 is a flow chart depicting an example method for presenting a sequence of medical images.

FIG. 5 is a flow chart depicting a method for presenting a sequence of medical images. At 502, optionally, one or more frames from the sequence of images is received by the client device 108. In some embodiments, the one or more frames are received and stored locally on storage 118 or memory 116 of client device 108. In other embodiments, one or more frames are received from data storage 104 or memory 116 on an on-demand basis or on an anticipatory basis. For example, the client device 108 may request a predefined number of frames to be transmitted from the data storage 104 to client device 108. In still other embodiments, the image sequence 404 is stored locally on client device 108. In still other embodiments, an initial amount of frames may be requested and received from data storage 104 to client device 108, and then one or more further requests for frames may be made at another point in time. In some embodiments, certain frames are pre-fetched based on the system determining the user's intention by monitoring the direction in which images are being navigated through.

In some embodiments, the one or more retrieved or received frames may be chosen in accordance with a pre-fetching algorithm which combines multiple strategies to determine which frames will be downloaded or received first. One strategy (referred to herein as a "shelf" strategy) is based on the proximity of frames to the currently displayed frame. For example, if frame #10 is being viewed and the direction is forward, frames #11-#14 will have increased priorities (the exact number of frames given an increase in weight by the shelf strategy may depend on the total number of frames in the image sequence). Likewise, frames #9 and #8 may also be given increased priorities, so as to ensure their availability if the user changes the direction of scrolling. The shelf strategy may ensure that frames will be displayed without lagging.

Another strategy (referred to herein as a "spike" strategy) involves selecting certain frames spread out through the sequence. In some embodiments, the spike frames are distributed evenly throughout the sequence. The spike frames may be downloaded and/or received in order to ensure that a minimum quantity of frames is available when navigating at a higher frame rate through the sequence (e.g., when certain frames may be skipped from being displayed altogether). The number of spikes chosen may depend on a number of factors, including available bandwidth, the total number of frames in the sequence, the maximum frame rate, or the like.

In some embodiments, background strategy may further select random frames from the sequence (e.g. using a random or lottery logic) to pre-fetch random frames from the sequence of images.

At 504, the client device 108 displays a first frame 404c from the sequence of images on display 124. The first frame 404c may be, for example, the beginning frame in the sequence of images. In some embodiments, the first frame 404c is the last frame in the sequence of images. In some embodiments, the first frame 404c is a frame which is neither the first nor the last frame in the sequence of images. In some embodiments, the user of client device 108 may select the first frame 404c to display by making a selection on the user interface using an input device (e.g. a mouse, a keyboard, a keypad, a touchscreen, or the like).

At 506, an instruction or indication is received from an input device to display additional frames from the sequence of images. In some embodiments, the input device is a linear input device. The instruction or indication may occur as, for example, a scroll wheel event (e.g. the scrolling of a scroll wheel on a pointing device), or a gesture made using a pointing device such as a mouse. Numerous different possible gestures are contemplated. For example, an instruction may include:

clicking and holding a mouse button while moving the cursor in a first direction (as depicted in FIG. 4, showing cursor clicked at 420a and dragged to location 420b), moving the cursor in a first direction within a designated area of the user interface (e.g. within the borders of the frame 404c being displayed), scrolling a scroll wheel or a trackball on a mouse or other pointing device, clicking and releasing a mouse button in a designated area of the user interface and moving the cursor away from the location in which the click occurred (as depicted in FIG. 4, showing the cursor icon changing to a different icon 430a and then being dragged to location 430b, with the cursor changing as the cursor is moved away from the initial clicking location), moving the cursor from within the boundaries of a displayed frame 404c to outside of the boundaries of the displayed frame 404c (as depicted in FIG. 4 with cursor locations 420a and 420b), tapping a touchscreen in a predefined area and then subsequently tapping in a location away from the original tapping location, and pressing and holding an arrow key on a keyboard or keypad device.

The aforementioned inputs are examples of instructions and/or indications to display additional frames from the sequence of medical images. Many more inputs and/or gestures from the user are possible to initiate the display of further frames. The above are merely examples. Moreover, the systems and methods described herein are operable to accept subsequent inputs, as described further below.

At 508, after receiving the instruction to display additional frames, the navigation system 126 determines a frame rate for displaying the additional frames. As described herein, the frame rate refers to the frequency at which each subsequent frame in the image sequence is displayed in the user interface 402. The frame rate may also be regarded as the length of time, or display period, for which each individual frame is displayed prior to a next frame being displayed in user interface 402.

The frame rate is determined based on a characteristic associated with the instruction or indication received from the user. In some embodiments, the characteristic is a cursor speed. For example, if a user clicks a mouse button and then moves the cursor, the frame rate may be determined on the basis of the cursor speed. Thus, in some embodiments, the faster the cursor is moved, the higher the frame rate. In some embodiments, the input movement speed may be normalized by the size of the viewing window. For example, the larger the viewing window, the faster the user would need to move the cursor to achieve the same frame rate.

In another example, the rotation of a scrolling wheel on a mouse is the characteristic. For example, when a user scrolls the scroll wheel for two increments (pointing devices often have notches in scroll wheels, such that an audible click or haptic feedback is provided with each increment, referred to as a "wheel scroll event"), each wheel scroll event is received by the navigation system. The navigation system is configured to receive wheel scroll events and determine whether more images should be displayed than the number of wheel scroll events that were created by the user. This allows for precision and speed in navigating through images, while reducing the burden on the user to provide a large number of wheel scroll events. Although each wheel scroll event is received as a linear event, the navigation system may interpret wheel scroll events linearly (when the user requires precision navigation), and/or non-linearly (when the user wishes to navigate quickly at a pre-defined frame rate). The systems and methods described herein may require less input movements from the user, and offer a better ergonomic experience with a lower chance of repetitive strain injuries for users.

In some embodiments, where the instruction or indication is movement of the cursor, the speed may be based on an inverse-logarithmic equation, such as speed=[direction of movement]$\times$base$^{input\_speed(log(max\_speed)-log(min\_speed))+log(min\_speed)}$, where the direction of movement is either +1 (e.g. a downward scrolling direction) or −1 (e.g. an upward scrolling direction).

In other embodiments, the frame rate may be based on a pre-defined frame rate. For example, if the user clicks the mouse within the boundaries of a currently displayed frame 404c, and then drags the cursor outside of the boundaries of the currently displayed frame 404c in user interface, the subsequent frames may be displayed at a pre-defined frame rate while the cursor is located outside of the boundaries of the frame. In some embodiments, the pre-defined frame rate is constant (that is, the location of the cursor once outside of the boundary of the frame 404c does not affect the frame rate). In some embodiments, the pre-defined frame rate is a pre-defined maximum frame rate. That is, the frame rate achieved may be lower than the pre-defined maximum frame rate if, for example, performance limitations of a client device or network connection do not allow for the maximum pre-defined frame rate to be achieved.

In still other embodiments, if the user presses and holds a key on a keyboard or keypad (e.g. pressing and holding one of the 'down', 'left', 'right', or 'up' keys), the subsequent frames may be displayed at a pre-defined maximum frame rate while the key is held down. In some embodiments, the additional pressing of a different key (e.g. pressing the 'up' key while the 'down' key continues to be held) may cause the frame rate to decrease, or stop the display of new frames temporarily.

In still other embodiments, if the user scrolls a scroll wheel, trackball or track pad, the frame rate for displaying the frames may be determined based on the rate at which the user is scrolling.

In still other embodiments, the if the user clicks a scroll wheel (e.g. on a mouse) and then moves the cursor away from the location at which the scroll wheel was clicked in the user interface 402, the frame rate may be determined based on a distance between the current cursor location and the location at which the scroll wheel was clicked.

In addition to the frame rate, the instruction and/or indication from the user to display additional frames may include a direction. The direction may determine whether to display frames which appear succeed the currently displayed frame 404c (e.g. displaying frames 404d, 404e, and so on, referred to hereinafter as a "forward" direction), or whether to display frames which precede the currently displayed frame 404c (e.g. displaying frames 404b, 404a, and so on, referred to hereinafter as a "reverse" direction). It will be appreciated that the image sequence may potentially be viewed in either the forward or reverse directions by a practitioner, and often areas of uncertainly in images may be reviewed repeatedly by a practitioner before arriving at a conclusion. As such, it is beneficial for the user to be able to easily and seamlessly change the direction in which the frames are being displayed without distracting the user with complicated mechanisms.

In some embodiments, the direction (e.g. forward or backward) for displaying frames may be determined by the direction of the cursor movement. For example, dragging the cursor to the right or vertically downward may cause the frames to be displayed in the forward direction, whereas dragging the cursor up or to the left may cause the frames to be displayed in reverse order.

In another example, scrolling a scroll wheel or trackpad in the 'up' direction may cause the frames to be displayed in the reverse direction, while scrolling in the 'down' direction may cause the frames to be displayed in the forward direction.

In embodiments in which the cursor is dragged from inside a boundary of a currently displayed frame 404*c* to outside of the boundary of the currently displayed frame 404*c*, the display direction may be based on the location of the cursor relative to the currently displayed frame 404*c*. For example, moving the cursor to an area to the left or vertically above the frame 404*c* may cause the frames to be displayed in reverse order. Moving the cursor to an area to the right of or vertically below the frame 404*c* may cause the frames to be displayed in forward order.

In embodiments in which a scroll wheel is clicked and then the cursor is moved away from the location in the user interface 402 in which the click occurred, moving the cursor vertically upward may result in displaying frames in the reverse direction, while moving the cursor vertically downward may cause frames to be displayed in the forward direction.

In each of the examples above, it should be noted that opposite directions can be substituted in alternative embodiments (e.g. moving down causes display in the reverse direction while moving up causes display in the forward direction). Numerous other configurations are possible and contemplated.

At 510, a second frame is displayed in user interface 402. In embodiments in which the frames are displayed in the forward direction, the second frame 404*d* is displayed after currently displayed frame 404*c*. In embodiments in which the frames are displayed in the reverse direction, the second frame 404*b* is displayed after currently displayed frame 404*c*.

The second frame is displayed in accordance with the frame rate or maximum frame rate determined at block 508. Accordingly, the second frame will be displayed for a pre-defined period of time, referred to as the display period. For example, if the frame rate is 5 frames per second, the display period would be 0.2 seconds per frame. At 512, it is determined whether the display period has elapsed. If the display period has not elapsed, then the method waits and returns to block 512.

When the display period has elapsed, then the method proceeds to block 514, at which the next frame is displayed. When the frames are being displayed in the forward direction, the order of frames from first to third may be frames 404*c*, 404*d* and then frame 404*e*. When frames are being displayed in the reverse direction, the order of display for the frames may be frames 404*c*, 404*b*, and then frame 404*a*.

At 516, it is determined whether there are any more frames to display. If there are more frames to display, the method returns to block 512, where it is determined whether the display period for the currently displayed frame has elapsed.

If there are no more frames to display, the method ends. For example, if the user has discontinued the instruction or indication to display additional frames, then the method will end. Discontinuing the instruction will depend on what the initial indication by the user was to initiate the displaying of additional frames. When the indication was pressing a mouse button and moving the cursor outside the boundary of frame 404*c*, then moving the cursor back within a displayed frame may cause the method to stop displaying additional frames. Alternatively, releasing the mouse button may cause the method to stop displaying additional frames, irrespective of the location of the cursor.

In some embodiments, if the user clicked within the boundary of a frame 404*c* and then dragged the cursor beyond the boundary of frame 404*c* (causing the frames to be displayed at a pre-defined frame rate), moving the cursor back within the boundary of the displayed frame may cause the frame rate to change from a pre-defined maximum frame rate to a frame rate which is based on the distance from the original clicking location in the user interface 402 to the current location of the cursor. As such, it is possible for the user to alternate between a constant frame rate and a variable frame rate depending on the location of the cursor.

In embodiments in which a keypad button is pressed and held or a scrolling wheel is being scrolled to initiate the display of additional frames, the displaying of additional frames can be stopped by releasing the keypad button or ceasing to engage the scroll wheel.

It should be appreciated that numerous methods can be used to cease the displaying of additional frames. These methods include but are not limited to performing the reverse of the action which acted as the input to trigger the displaying of additional frames.

In some embodiments, if all of the frames in the sequence have been displayed up to the final (or beginning) frame in the sequence, then the method may end. In some embodiments, the method may loop back to the beginning (or end) of the frames in the image sequence when the end has been reached. For example, if displaying in reverse order, after displaying frame 404*a*, the system may loop around to end of the image sequence and display frame 404*f*.

In some embodiments, the navigation system 126 is operable to accept one or more indications from a user subsequent to the initial indication that additional frames should be displayed. For example, if the initial indication from the user was to display additional frames in the forward direction, a user may subsequently provide an indication that modifies the original indication. For example, the user may provide an indication to reduce or increase the frame rate (e.g. by moving a cursor closer to or further away from an original location of the clicking and holding of a mouse button). Moreover, the user may move a cursor in a different or opposite direction from the original indication, which may cause the method to display frames in an opposite direction (e.g. from forward to reverse, or vice versa) than the original direction.

Figure 6:
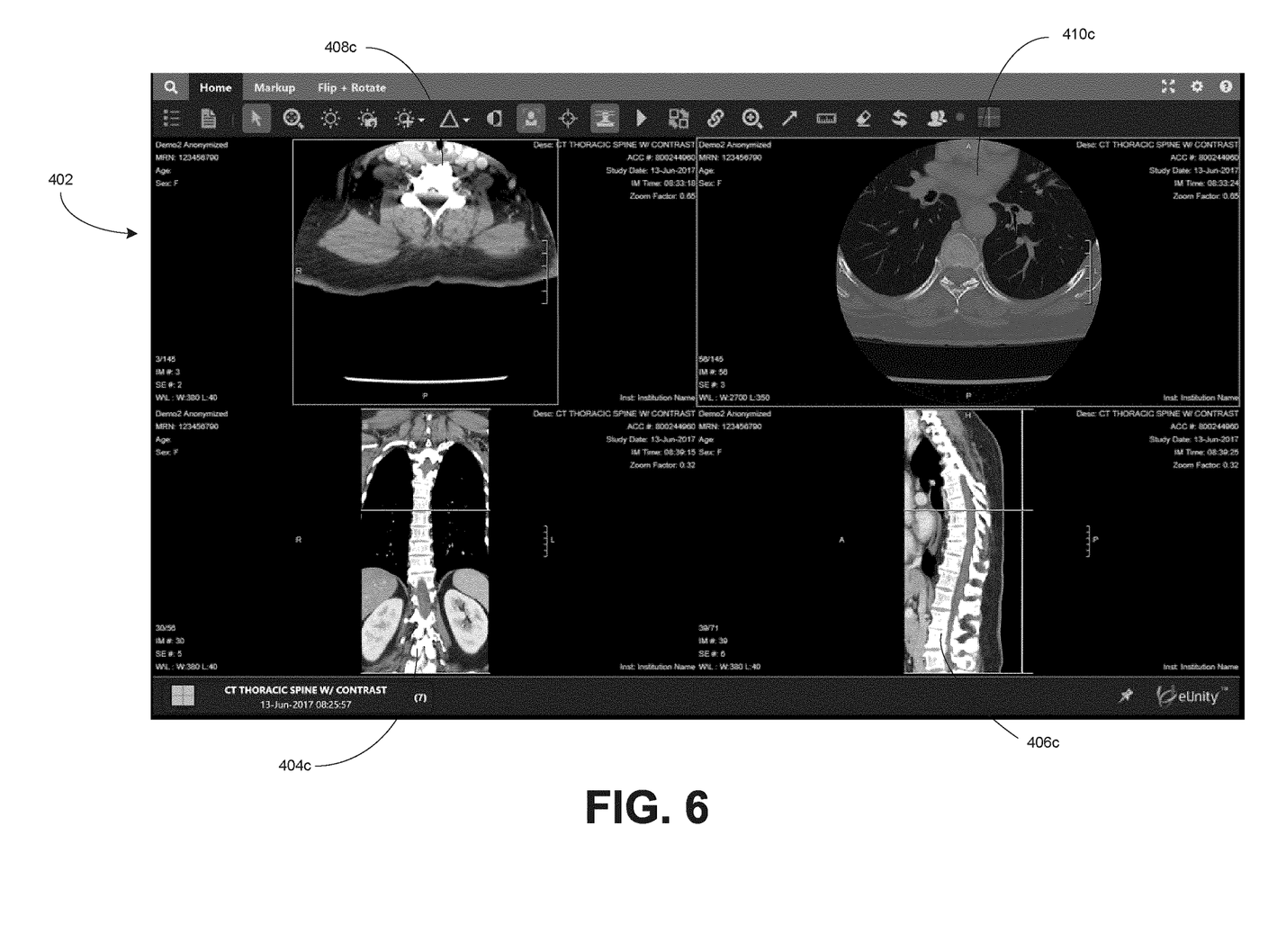
FIG. 6 depicts another example user interface of a navigation system.

FIG. 6 depicts an example user interface 402 of navigation system 126. As depicted, the user interface 402 is operable to display four sets of related medical image sequences 404, 406, 408, 410 simultaneously. It will be further noted that relative to FIG. 4, there is no thumbnail view of any of the frames of a sequence in the user interface depicted in FIG. 6.

Figure 7:
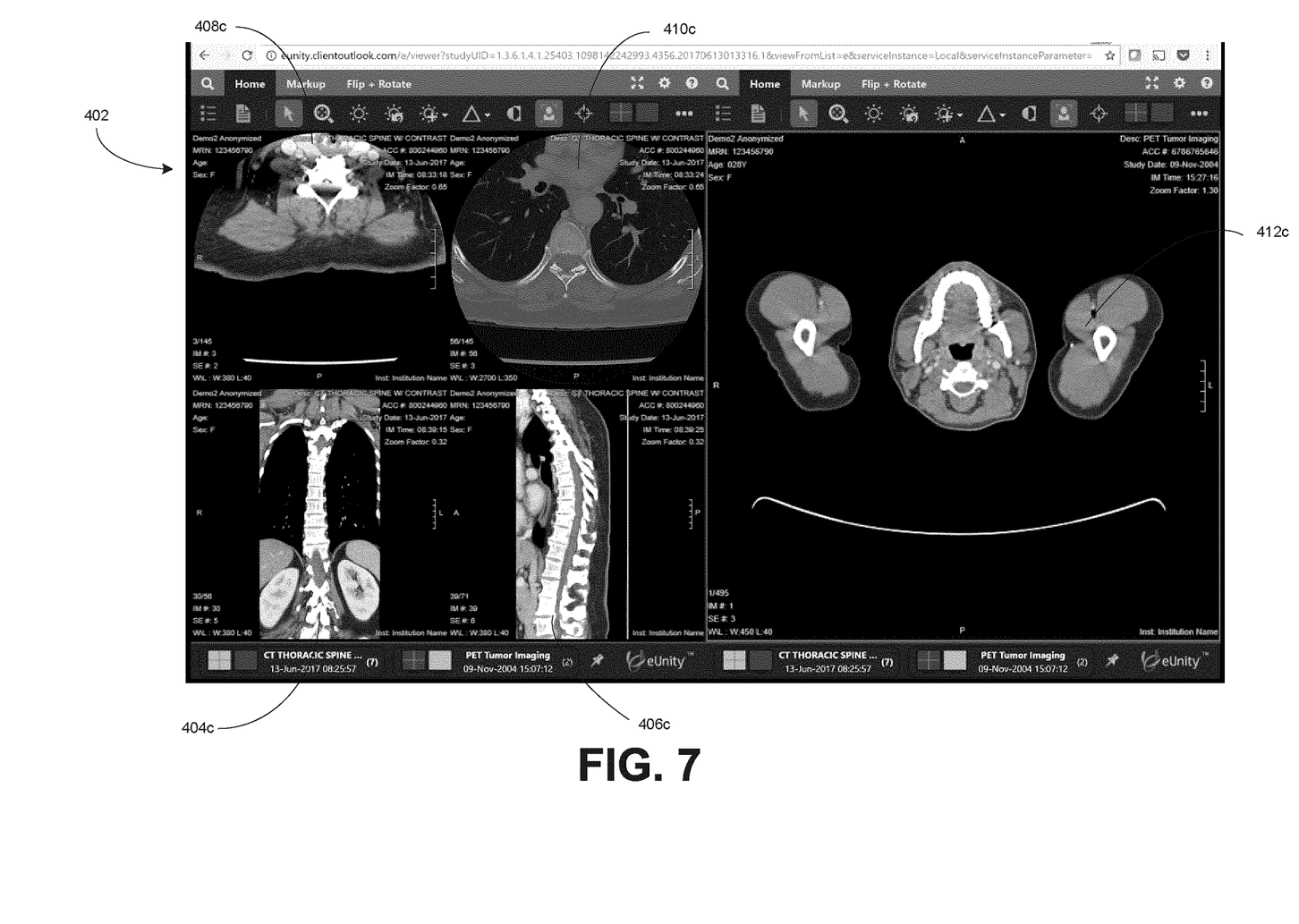
FIG. 7 depicts yet another example user interface of a navigation system.

FIG. 7 depicts an example user interface 402 of navigation system 126. As depicted, the user interface 402 is operable to display five sets of related medical image sequences 404, 406, 408, 410, 412 simultaneously. It will be appreciated that in some embodiments, one or more image sequences may be presented with a larger viewing area. As depicted, frame 412*c* is displayed using more screen area than any of frames 404*c*, 406*c*, 408*c*, and 410*c*. In embodiments which display more than one set of frames at a time, the user may place a cursor within any of the displayed frames in order to provide an indication that additional frames should be displayed.

In some embodiments, the navigation system 126 display successive frames without omitting any intermediate frames. Thus, in FIG. 4, the system 126 would display each of frames 404a, 404b, 404c, 404d, 404e and 404f in succession (or in the reverse order) without any omissions. Thus, frames are displayed in consecutive order in user interface 402.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

The following discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be at least partly in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

Although specific embodiments have been described in detail, it should be understood that various changes, substitutions and alterations can be made. The invention is therefore defined by the claims.

What is claimed is:

1. A method of presenting a plurality of frames from a sequence of medical images at a client device, the method comprising:
    displaying, on a display device, a first frame from a sequence of images;
    receiving, via an input device, an indication to display at least second and third adjacent frames from the sequence of images, wherein the indication is a movement of a pointing device outside of a boundary of the first frame in a user interface;
    determining a frame rate for displaying the at least second and third adjacent frames based on the indication received from the input device;
    displaying, on the display device, the at least second and third adjacent frames in accordance with the frame rate.

2. The method of claim 1, wherein the at least second and third adjacent frames immediately succeed the first frame in the sequence of images.

3. The method of claim 1, wherein the at least second and third adjacent frames immediately precede the first frame in the sequence of images.

4. The method of claim 1, wherein the indication is a command to scroll in a first direction at a first rate.

5. The method of claim 1, wherein the indication is a movement of a pointing device in a first direction at a first speed.

6. The method of claim 1, wherein the at least second and third frames are displayed at a frame rate less than or equal to a predefined maximum frame rate when the pointing device is outside of the boundary of a frame being displayed.

7. The method of claim 1, wherein the indication is a pressing and holding of a key on the input device.

8. The method of claim 1, wherein the received indication is a first indication, and wherein the method comprises:
    receiving a second indication subsequent to the first indication.

9. The method of claim 8, further comprising:
    modifying the frame rate based on the second indication.

10. A computing device for presenting frames of a sequence of medical images, the computing device comprising:
    a processor;
    a display device;
    an input device;
    a memory having stored thereon processor-executable instructions for:
        displaying, on the display device, a first frame from a sequence of images;
        receiving, via the input device, an indication to display at least second and third adjacent frames from the sequence of images, wherein the indication is a movement of a pointing device outside of a boundary of the first frame in a user interface;
        determining a frame rate for displaying the at least second and third adjacent frames based on the indication received from the input device;
        displaying, on the display device, the at least second and third adjacent frames in accordance with the frame rate.

11. A system for presenting a sequence of medical images, the system comprising:
    a server comprising a processor and a memory storing a sequence of medical images comprising a plurality of frames; and
    a client device comprising:
        a processor;
        a network interface;
        a display device;
        an input device;
        a memory having stored thereon processor-executable instructions for:
            receiving, via the network interface, two or more frames of the sequence of medical images;
            displaying, on the display device, a first frame from the received sequence of images;
            receiving, via the input device, an indication to display at least second and third adjacent frames from the received sequence of images, wherein the indication is a movement of a pointing device outside of a boundary of the first frame in a user interface;

determining a frame rate for displaying the at least second and third adjacent frames based on the indication received from the input device; and displaying, on the display device, the at least second and third adjacent frames in accordance with the frame rate.

12. The method of claim 1, wherein the frame rate for displaying the at least second and third adjacent frames is based on a characteristic associated with the indication received from the input device.

13. The computing device of claim 10, wherein the frame rate for displaying the at least second and third adjacent frames is based on a characteristic associated with the indication received from the input device.

14. The system of claim 11, wherein the frame rate for displaying the at least second and third adjacent frames is based on a characteristic associated with the indication received from the input device.

15. The computing device of claim 10, wherein the at least second and third frames are displayed at a frame rate less than or equal to a predefined maximum frame rate when the pointing device is outside of the boundary of a frame being displayed.

16. The computing device of claim 11, wherein the at least second and third frames are displayed at a frame rate less than or equal to a predefined maximum frame rate when the pointing device is outside of the boundary of a frame being displayed.

* * * * *